United States Patent [19]
Clover, Jr.

[11] Patent Number: 4,756,712
[45] Date of Patent: Jul. 12, 1988

[54] KNEE JOINT ASSEMBLY

[75] Inventor: William M. Clover, Jr., Trabuco Canyon, Calif.

[73] Assignee: Orthomedics, Inc., Brea, Calif.

[21] Appl. No.: 892,965

[22] Filed: Aug. 4, 1986

[51] Int. Cl.⁴ .............................................. A61F 2/62
[52] U.S. Cl. .................................................. 623/39
[58] Field of Search .......... 16/326, 332, 381, 389–392; 623/27, 39–46; 135/112, 113, 69, 74, 99, 109, 106, 114; 403/92, 93, 100, 102

[56] References Cited

U.S. PATENT DOCUMENTS

| | | | |
|---|---|---|---|
| 4,111,217 | 9/1978 | Victor | 135/109 |
| 4,283,800 | 8/1981 | Wilson | 623/39 |
| 4,286,353 | 9/1981 | Roche | 403/102 |
| 4,602,627 | 7/1986 | Vito | 623/39 |
| 4,602,889 | 7/1986 | Mu-Shan | 403/93 |
| 4,614,518 | 9/1986 | Lehneis | 623/39 |

Primary Examiner—Richard J. Apley
Assistant Examiner—James Prizant
Attorney, Agent, or Firm—Nilsson, Robbins, Dalgarn, Berliner, Carson & Wurst

[57] ABSTRACT

A knee joint assembly utilized in an above knee prosthesis includes an upper half member, a lower half member, and a locking pin assembly for locking the upper and lower half members together. The upper member has a front face having a lower edge, a center rib which is orthogonal to the front face, and two upper surfaces, one on each side of the center rib. The two upper surfaces are each upwardly sloped from the front to the rear of the upper member when the upper member is locked together with the lower member. The lower member includes a base having a lip protruding horizontally. The lower member also includes two ramps extending parallel to each other and extending vertically from the base. The ramps each have a sloped surface. When the upper and lower members are locked together, the two ramp surfaces contact the two upper surfaces, the front face edge contacts the lip of the base, and the front part of the center rib contacts a part of the base, thereby providing a substantial amount of contact surface between the upper and lower half members.

9 Claims, 2 Drawing Sheets

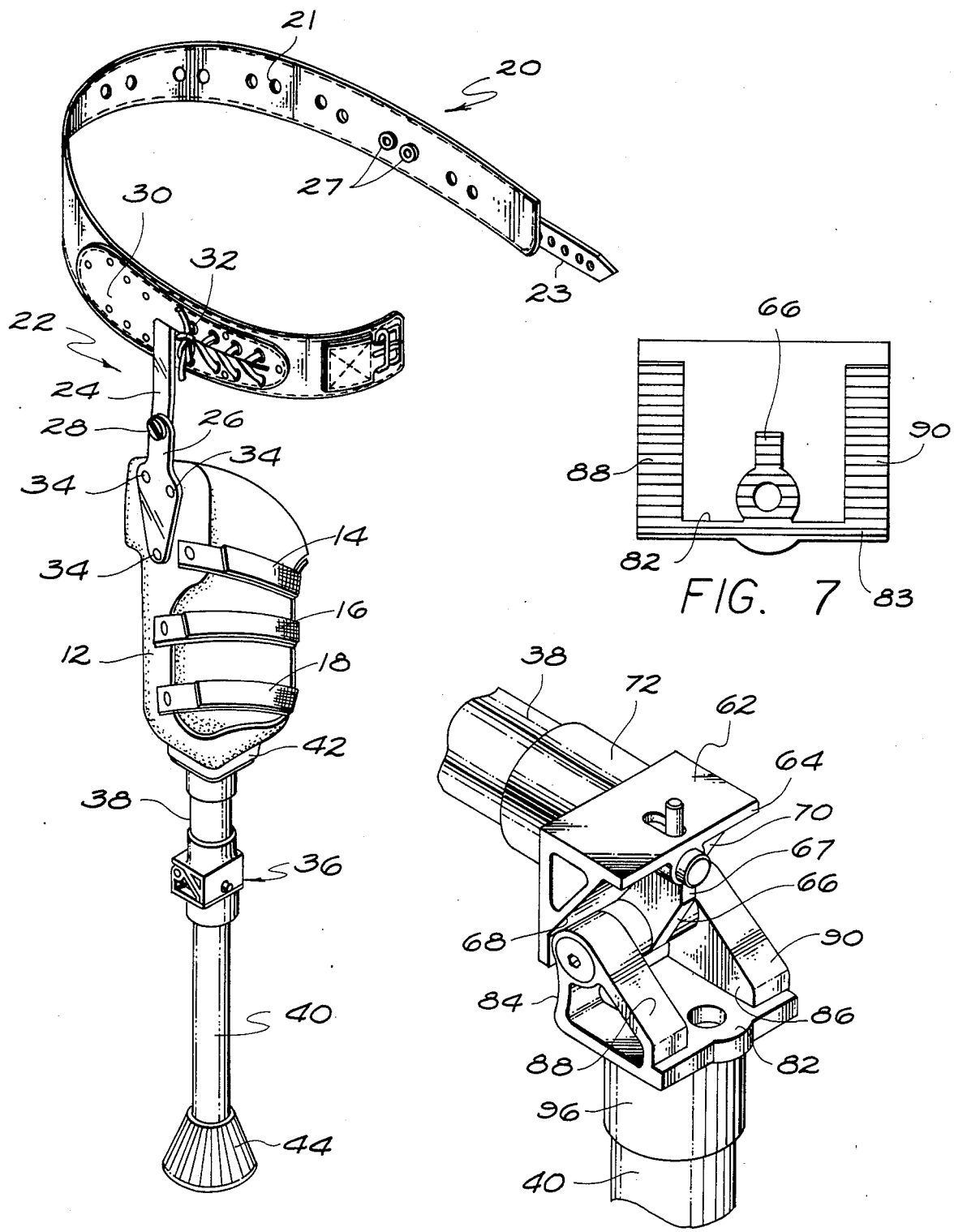

KNEE JOINT ASSEMBLY

BACKGROUND OF THE INVENTION

The present invention relates to prosthetic devices and, more particularly, to a knee joint assembly for an above knee prosthesis that has a significantly large surface contact area between the two half members of the knee joint assembly to distribute the load and stress forces across a large surface area in order to reduce the wear of the knee joint assembly.

Prior knee joint assemblies have been manufactured in metal and are generally comprised of two half members pivotally mounted to each other. Usually a locking pin assembly is utilized to lock the two halves together. In some prior devices, attached to one half member are two plastic discshaped pucks. The pucks are attached very near the locking pin and engage the base of the other half member when the two halves are locked together. However, only a small portion of each puck circumference engages the base.

When a person walks or stands while wearing the above knee prosthesis, the stress and load forces are transferred through the prosthesis to the knee joint assembly and specifically to the area of contact between the two half members. Of course, the two halves are locked to each other during these types of activities. Therefore, the load and stress forces are transferred to the puck circumference area which engages the base. After a period of time this causes the puck circumference area to deform which allows movement between the two half members even when they are locked together. This causes instability of the prosthesis. Therefore, the person will then either obtain a new prosthesis or knee joint assembly, or continue using the prosthesis, thereby jeopardizing his or her safety.

People in third world countries who require above knee prostheses need a prosthesis which will last long, is inexpensive, can be adjusted immediately, and is lightweight. Additionally, since these people usually perform more manual labor than others, the stress and load forces applied to the prosthesis is increased. Therefore, the prosthesis will become unstable sooner and since these people usually are very poor, they will continue to use the unsafe prosthesis. Furthermore, since many of these people live in remote areas or where clinics and hospitals are far, they need a prosthesis which can be adjusted for them where they are located.

The present invention is a knee joint assembly which is lightweight and provides a substantially larger area of surface contact between the two half members. This increases the distribution of load and stress forces, thereby reducing the wear and increasing the longevity of the knee joint assembly.

SUMMARY OF THE INVENTION

A knee joint assembly utilized in an above knee prosthesis which includes above and below knee portions. The knee joint assembly is coupled between the above and below knee portions. The knee joint assembly comprises a first half member, a second half member pivotally mounted to the first half member, and a locking pin assembly for locking the first and second half members together. The first and second half members contact each other such that the ratio of horizontal cross-sectional surface area of contact between the first and second half members is at least forty percent (40%) of the total horizontal cross-sectional surface area when the first and second half members are locked together.

BRIEF DESCRIPTION OF THE DRAWINGS

The invention will be better understood from the following detailed description thereof taken in conjunction with the accompanying drawings, in which:

FIG. 1 is a view of the present invention utilized in an above knee prosthesis;

FIG. 2 is a perspective view of the present invention;

FIG. 7 is a horizontal cross-sectional view taken along line 7—7 of FIG. 4 showing the surface ares of contact between the first and second half members when they are locked together.

DETAILED DESCRIPTION OF THE PREFERRED EMBODIMENT

Figure 3:
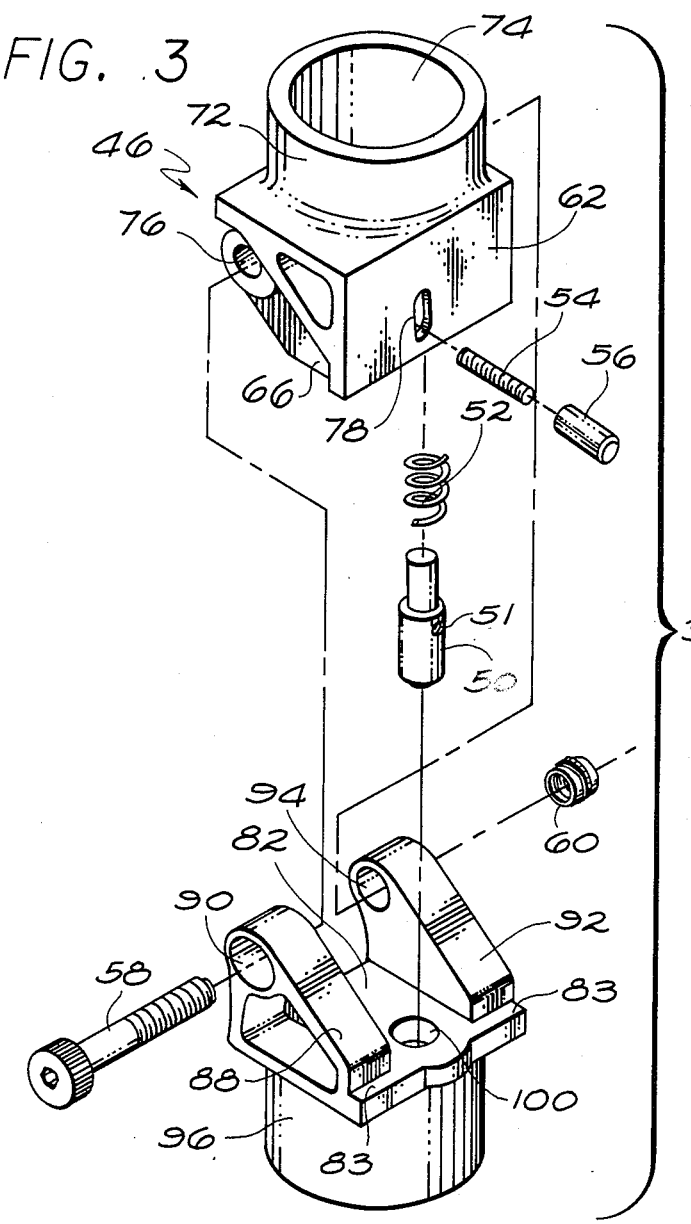
FIG. 3 is an exploded view of the present invention.

Referring to FIG. 1, an above knee prosthesis utilizing the knee joint assembly of the present invention is shown. The prosthesis includes an above knee portion which includes a socket 12 for receiving a person's upper leg. Although not shown, the socket 12 comprises two pieces which partially overlap each other thereby allowing the socket to be adjustable. Straps 14, 16 and 18 tighten the socket 12 around the upper leg. The straps can be of the belt and buckle type, or hook and pile fasteners such as those sold under the trademark "Velcro", as shown in the preferred embodiment. Each of the pile ends of the straps are riveted to one side of the socket while the hook ends of each strap are threaded through D-rings (not shown) attached to the other side of the socket, and doubled back onto themselves to be fastened on the pile ends.

The above knee portion further includes a belt 20 which wraps around the person's waist thereby securing the prosthesis to the person. The belt 20 is constructed such that portions of it may be cut away to fit various waist sizes. However, cutting away portions of the belt will not separate the various layers which comprises the belt which are stiched together. Furthermore, the belt includes perforations 21 along the length of the belt to allow the belt tongue 23, which engages the buckle 25, to be placed at various locations on the belt utilizing Chicago-type screws 27. This further allows adjustment for various waist sizes.

The socket 12 is attached to the belt 20 by a pelvic pivot guide 22. The pelvic pivot guide 22 comprises a first rigid bar 24 and a second rigid bar 26 which are pivotally attached to each other by screw 28 and nut (not shown). The first bar 24 is placed in a belt pocket 30 which includes a plurality of holes for receiving a lace 32. When the first bar 24 is placed in the belt pocket 30, the lace 32 is pulled to tighten the pocket 30 around the first bar 24. The lace is then tied into a knot to secure the first bar 24 in the belt pocket 30. The second bar 26 is mounted to the socket 12 by rivets 34.

The upper knee portion includes a first rigid tube 38 attached, by glue or the like, to a connector 42 which is mounted to the socket 12 by screws and nuts (not shown). The knee joint assembly 36 of the present invention is disposed between the first rigid tube 38 and a below knee portion which includes a second rigid tube 40. The below knee portion also includes a pylon 44 mounted to the second rigid tube 40. A foot structure may be substituted for pylon 44. However it has been shown that the use of the pylon 44 is more versatile in third world countries.

The socket 12, pelvic pivot guide 22, connector 42, pylon 44 and the majority of the knee joint assembly 36 are constructed of injection molded plastic thereby yielding a prosthesis which is strong, lightweight, inexpensive and easily adjustable.

Referring to FIGS. 2 and 3, the knee joint assembly 36 includes an upper half member 46 and a lower half member 48. Each half member is unitary and made from injection molded plastic. A locking pin assembly comprising a locking pin 50, spring 52, threaded screw 54 and screw cover 56 are disposed in the upper half member 46 as will be described later. A pivot screw 58 is disposed through the rear portions of the upper half member 46 and lower half member 48, and threaded into nut 60, thereby pivotally mounting the upper half member 46 and lower half member 48 to each other.

Figure 4:
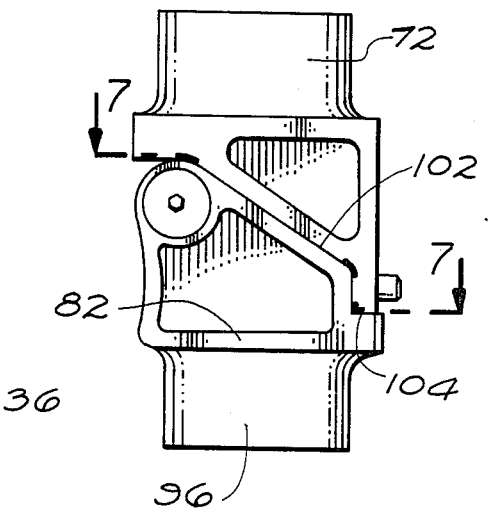
FIG. 4 is a side elevational view of the present invention.

The upper half member 46 includes a front face 62 which has a lower edge 64. A rib 66 is disposed centrally of the upper half member 46 and orthogonally to the front face 62. The upper half member 46 further includes a first sloped upper surface 68 and a second sloped upper surface 70, disposed so that the central rib 66 extends from and between the first and second upper surfaces 68 and 70. When the upper half member 46 is in the locking position, as shown in FIG. 4, the first and second upper surfaces 68 and 70 are sloped upwardly from front to rear.

An upper cylindrical extension 72 protrudes upwardly from the top surface of the upper half member 46, and has a recess 74 therein for receiving the first rigid tube 38. An aperture 76 is formed at the rear portion of the center rib 66.

Figure 6:
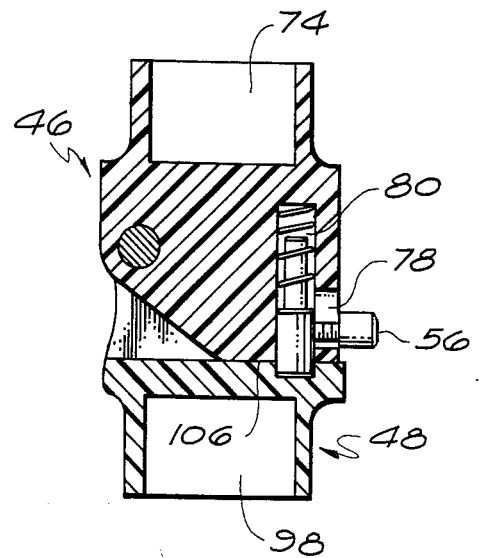
FIG. 6 is a cross-sectional side view of the present invention taken along line 6—6 of FIG. 5.

In order to accomodate the locking pin assembly, the upper half member 46 includes a second aperture 78 formed on the front face 62, and a second recess 80 formed in the front part of the center rib 66 adjacent to the front face 62 (FIG. 6). The spring 52 is placed in the second recess 80 with the locking pin 50 following the spring 52. The threaded screw 54 is then passed through the aperture 78 and threaded into the bore 51 of the locking pin 50. The screw cover 56 is then threaded on the exterior end of threaded screw 54 thereby, yielding the locking pin assembly as illustrated in FIGS. 3 and 6.

The lower half member 48 includes a base 82 having a horizontal lip 83, a first ramp 84 and a second ramp 86. The first ramp 84 has a sloped surface 88 and an aperture 90. The second ramp 86 has a second sloped surface 92 and a second aperture 94. A lower cylindrical extension 96 depends from the bottom of the lower half member 48 and has a recess 98 formed therein for receiving the second rigid tube 40. A second recess 100 for receiving the locking pin 50 is formed in the base 82 between the first ramp 84 and the second ramp 86.

The pivot screw 58 is passed through the first ramp aperture 90 then through the center rib aperture 76 and finally through the second ramp aperture 94. The nut 60 is then threaded on the pivot screw 58 thereby pivotally mounting the upper half member 46 to the lower half member 48 and yielding the knee joint assembly as shown in FIG. 2. The spring 52 urges the locking pin 50 toward the lower half member 48. However, since the threaded screw 54 extends through the aperture 78 and is threaded into the locking pin 50, the movement of the locking pin 58 is limited by the size of the aperture 78. The upper half member 46 is locked together with the lower half member 48 when the locking pin 50 engages within the base recess 100.

Figure 5:
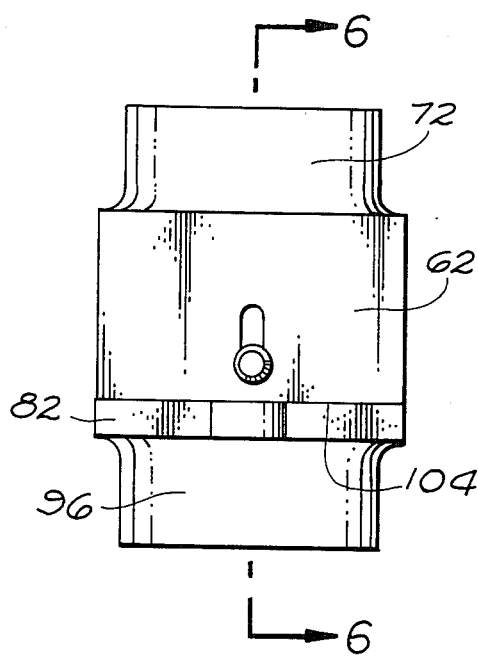
FIG. 5 is a front elevational view of the present invention.

Referring to FIG. 4, the first upper sloped surface 68 contacts the first ramp sloped surface 88 as shown at 102 when the knee joint assembly 36 is in the locking position. The second upper sloped surface 70 contacts the second ramp sloped surface 92 in a similar manner. Additionally, the entire front face edge 64 contacts the base lip 83 as shown at 104 in FIGS. 4 and 5. The front part 67 of the center rib 66 also contacts the base 82 and is shown at 106 in FIG. 6. Therefore, the contact surface areas between the upper half member 46 and lower half member 48 includes the surface area of the first ramp sloped surface 88, the second ramp sloped surface 90, the front face edge surface 64 and the front part 67 of the center rib which contacts the base 82 as shown at 106. This total contact surface area is significantly larger than knee joint assemblies currently made.

If the contact area between the upper half and the lower half was projected on a horizontal cross-section, such as about line 7—7 in FIG. 4, the result would be as shown in FIG. 7. The shaded areas indicate the areas of contact between the two halves. In the preferred embodiment, the ratio of the shaded area and the total area shown in FIG. 7 is approximately sixty two percent (62%) of the total horizontal cross sectional area. However, the knee joint assembly will function as described with a ratio as low as forty percent (40%). Current knee joint assemblies have a ratio of less than five percent (5%).

Therefore, the load forces applied to the lower half member 48 by the upper half member 46 is distributed over a larger surface area compared to those currently. This significantly increases the longevity of the knee joint assembly by reducing the amount of surface material worn away between the upper half member 46 and lower half member 48. Additionally since the knee joint assembly is made from injection molded plastic, the knee joint assembly is lightweight.

From the foregoing, it has been shown that the present invention provides a knee joint assembly which is lightweight, inexpensive and significantly increases the surface contact area between the upper half member and lower half member thereby reducing the wear of the knee joint assembly and increasing the longevity of the knee joint assembly. Although a specific embodiment has been illustrated and described, various modifications and changes may be made without departing from the spirit and scope of the invention.

What is claimed is:

1. A knee joint assembly for simulating a human knee joint in an above knee prosthesis, the prosthesis including above and below knee portions with the knee joint assembly coupled between the above and below knee portions, the knee joint assembly comprising:

a first half member;

a second half member pivotally mounted to said first half member;

a locking pin assembly for locking said first and second half members together;

said first and second half members being adapted to contact each other in such a manner that the ratio of horizontal cross-sectional area of contact between said first and second half members is at least forty precent (40%)) of the total horizontal cross-sectional surface area when said first and second half members are locked together;

said second half member being of unitary construction and comprising:
 a base;
 a first ramp having a sloped surface, and
 a second ramp having a sloped surface, said first and second ramps extending vertically from said base and parallel to each other;

said first half member further having a recess formed therein, and a first aperture connected to said recess;

said locking pin assembly comprising:
 a locking pin disposed in said rib recess;
 means for biasing said locking pin out of said recess;
 a connecting member placed through said aperture and connected to said locking pin thereby limiting the movement of said locking pin in said recess;

said base further having a recess formed therein for receiving said locking pin when said upper and lower half members are locked together;

said first half member further having a second aperture formed therein near the rear portion fo said first half member;

said first ramp further having an aperture formed therein;

said second ramp further having an aperture formed therein; and said knee joint assembly further comprising a pivot connecting member disposed through said first ramp aperture, said first half member second aperture and said second ramp aperture, thereby pivotally mounting said first and second half members together.

2. A knee joint assembly for simulating a human knee joint in an above knee prosthesis, the prosthesis including an above and a below knee portion with the knee joint assembly coupled between the above and below knee portions, the knee joint assembly comprising:
 a first half member of unitary construction, comprising;
  a front face having a lower edge,
  a rear portion,
  a central rib extending between said front face and said rear portion and being disposed orthogonally to said front face,
  first and second supper surfaces sloping from said front face to said rear portion, on either side of said rib;
 a second half member of unitary construction, comprising;
  a base,
  a first ramp having a sloped surface,
  a second ramp having a sloped surface, said sloped surfaces of said first and second ramps being coplanar;
 said first ramp sloped surface being adapted to contact said first upper surface, said second ramp sloped surface being adapted to contact said second upper surface, said front face edge being adapted to contact said base and a part of said rib being adapted to contact said base when said first and second half members are locked together, thereby yielding a ratio of horizontal cross-sectional surface area of contact between said first and second half members of at least forty percent (40%) of the total horizontal cross sectional surface area;

said rib having a recess formed therein near said front face;

said front face having an aperture connected to said rib recess;

a locking pin assembly for locking said first and second half members together, said locking assembly comprising;
 a locking pin disposed in said rib recess,
 a spring disposed between said locking pin and rib recess to urge said locking pin out of said rib recess,
 a screw secured through said front face aperture to one end of said locking pin to limit the movement of said locking pin in said rib recess, and
 a screw cover secured to the other end of said threaded screw;

said base having a recess formed therein for receiving said locking pin when said upper and lower half members are locked together;

said rib having an aperture formed therein near the rear portion of said first half member;

said first and second ramps having apertures formed therein;

a pivot screw positioned in said rib aperture, and said first and second ramp apertures; and a nut secured to one end of said pivot screw, thereby pivotally mounting said first and second half members together.

3. A knee joint assembly from simulating a human knee joint in an above knee prosthesis, the prosthesis including above and below knee portions with the knee joint assembly coupled between the above and below knee portions, the knee joint assembly comprising:
 a first half member of unitary construction, comprising;
  a front face having a lower edge,
  a rear portion,
  a rib disposed centrally of said first half member and orthogonally to said front face, and
  first and second surfaces sloping upwardly from said front face to said rear portion, said first and second surfaces being positioned on each side of said rib;
 a second half member of unitary construction comprising;
  a base,
  a first ramp having a sloped surface, and
  a second ramp having a sloped surface, said first and second ramps extending vertically from said base and parallel to each other; and
 a locking pin assembly for locking said first and second half members together; and
 said first ramp sloped surface being adapted to contact said first upper surface, said second ramp sloped surface being adapted to contact said second upper surface, said front face edge being adapted to contact said base and a part of said rib being adapted to contact said base when said first and second half members are locked together, thereby yielding a ratio of horizontal cross sectional surface area of contact between said first and second half members of at least forty percent (40%) of the total horizontal cross-sectional surface area.

4. A knee joint assembly for simulating a human knee joint in an above knee prosthesis, the prosthesis including above and below knee portions, the knee joint assembly comprising:
- a first half member attached to one portion;
- a second half member pivotally mounted to said first half member and attached to the other portion;
- a locking pin assembly for locking said first and second half members together thereby forming a common longitudinal axis through the two portions; and
- said first and second half members having opposed, adjacent sloped surfaces forming an area of contact between said first and second half members when said first and second half members are locked together, so that stress on said pivotal mounting and on said locking pin, occurring when one portion of the prosthesis is rotated about the longitudinal axis relative to the other portion, is partially relieved through the action of one sloped surface bearing on the other.

5. The knee joint assembly as defined in claim 1 wherein said first half member is of unitary construction and includes:
- a front face having a lower edge;
- a rear portion;
- a weight bearing rib disposed orthogonally to said front face portion; and
- first and second surfaces sloping upwardly from said front face to said rear portion, said first and second surfaces being positioned on each side of said rib.

6. The knee joint assembly as defined in claim 5 wherein:
- said rib of the first half member is disposed centrally of said first half member and has a recess formed therein near said front face;
- said front face has an aperture connected to said rib recess;
- said locking pin assembly comprises;
  - a locking pin disposed in said rib recess, means for biasing said locking pin out of said rib recess, and a connecting member placed through said front face aperture and connected to said locking pin thereby limiting the movement of said locking pin in said rib recess; and
- said second half member further has a recess formed therein for receiving said locking pin when said first and second half members are locked together.

7. The knee joint assembly as defined in claim 6 wherein:
- said rib has an aperture formed therein near the rear portion of said first half member;
- said second half member further has a first and second aperture formed therein; and
- said knee joint assembly further comprises a pivot connecting member disposed through said second half member first aperture, said rib aperture and said second half member second aperture, thereby pivotally mounting said first and second half members together.

8. The knee joint assembly as defined in claim 1 wherein said second half member is of unitary construction and includes:
- a base;
- a first ramp having a sloped surface, and
- a second ramp having a sloped surface; said first and second ramps extending vertically from said base and parallel to each other.

9. The knee joint assembly as defined in claim 8 wherein:
- said first half member further includes a recess formed therein, and a first aperture having a path connected to said recess;
- said locking pin assembly comprises;
  - a locking pin disposed in said rib recess; and means for biasing said locking pin out of said recess; and
  - a connecting member placed through said aperture and connected to said locking pin thereby limiting the movement of said locking pin in said recess; and
- said base further having a recess formed therein for receiving said locking pin when said upper and lower half members are locked together.

* * * * *

UNITED STATES PATENT AND TRADEMARK OFFICE
CERTIFICATE OF CORRECTION

PATENT NO. : 4,756,712
DATED : July 12, 1988
INVENTOR(S) : William M. Clover, Jr.

It is certified that error appears in the above-identified patent and that said Letters Patent is hereby corrected as shown below:

Column 2, line 19, delete "ares", and insert --areas--

Column 2, line 47, delete "stiched", and insert --stitched--

Signed and Sealed this

Sixth Day of December, 1988

Attest:

DONALD J. QUIGG

*Attesting Officer*    *Commissioner of Patents and Trademarks*